United States Patent
Mehta et al.

(10) Patent No.: US 11,147,758 B2
(45) Date of Patent: Oct. 19, 2021

(54) COSMETIC COMPOSITION COMPRISING NON-AMINO POLYALKYLSILOXANES, OXYETHYLENATED POLYMERS AND FATTY ALCOHOLS

(71) Applicant: L'OREAL, Paris (FR)

(72) Inventors: Khyati Mehta, Maharashtra (IN); Maxime De Boni, Maharashtra (IN); Harshada Tulsyan, Maharashtra (IN)

(73) Assignee: L'OREAL, Paris (FR)

( * ) Notice: Subject to any disclaimer, the term of this patent is extended or adjusted under 35 U.S.C. 154(b) by 256 days.

(21) Appl. No.: 15/563,787

(22) PCT Filed: Mar. 31, 2016

(86) PCT No.: PCT/EP2016/057050
§ 371 (c)(1),
(2) Date: Oct. 2, 2017

(87) PCT Pub. No.: WO2016/156486
PCT Pub. Date: Oct. 6, 2016

(65) Prior Publication Data
US 2018/0078488 A1 Mar. 22, 2018

(30) Foreign Application Priority Data

Apr. 2, 2015 (IN) .............................. 952/DEL/2015

(51) Int. Cl.
| | | |
|---|---|---|
| *A61Q 5/06* | (2006.01) | |
| *A61K 8/898* | (2006.01) | |
| *A61K 8/34* | (2006.01) | |
| *A61Q 5/12* | (2006.01) | |
| *A61K 8/86* | (2006.01) | |
| *A61K 8/891* | (2006.01) | |
| *A61Q 5/02* | (2006.01) | |

(52) U.S. Cl.
CPC .............. *A61K 8/898* (2013.01); *A61K 8/342* (2013.01); *A61K 8/86* (2013.01); *A61K 8/891* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,589,578 A | 6/1971 | Kamphausen |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,165,367 A | 8/1979 | Chakrabarti |
| 4,172,887 A | 10/1979 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,591,610 A | 5/1986 | Grollier |
| 4,761,273 A | 8/1988 | Grollier et al. |
| 4,996,059 A | 2/1991 | Grollier et al. |
| 5,089,252 A | 2/1992 | Grollier et al. |
| 5,374,421 A | 12/1994 | Tashiro et al. |
| 6,235,275 B1 | 5/2001 | Chen et al. |

(Continued)

FOREIGN PATENT DOCUMENTS

| | | |
|---|---|---|
| EP | 0080976 A1 | 6/1983 |
| EP | 0122324 A1 | 10/1984 |

(Continued)

OTHER PUBLICATIONS

DOW Corning 2502 Fluid Aug. 23, 2012 (Year: 2012).*
International Search Report for PCT/EP2016/057050 dated Jun. 7, 2016.
Written Opinion for PCT/EP2016/057050 dated Jun. 7, 2016.

*Primary Examiner* — Jyothsna A Venkat

(74) *Attorney, Agent, or Firm* — The Marbury Law Group, PLLC

(57) ABSTRACT

The present invention relates to a cosmetic composition comprising one or more particular non-amino polyalkylsiloxanes comprising at least one fatty chain, one or more oxyethylenated polymers and one or more fatty alcohols. The invention also relates to a cosmetic treatment process of keratin materials, and particularly a method for conditioning keratin fibres, and in particular human keratin fibres, using this composition.

5 Claims, No Drawings

(56) References Cited

U.S. PATENT DOCUMENTS

| | | |
|---|---|---|
| 6,451,300 B1 | 9/2002 | Dunlop et al. |
| 6,706,674 B2 | 3/2004 | Cincotta et al. |
| 8,038,989 B2 * | 10/2011 | Murray ............... A61K 8/0295 424/70.27 |
| 8,658,140 B2 | 2/2014 | Nguyen et al. |
| 2004/0062740 A1 | 4/2004 | Fan et al. |
| 2005/0196372 A1 | 9/2005 | Cajan et al. |
| 2008/0311067 A1 | 12/2008 | Murray et al. |
| 2009/0074700 A1 * | 3/2009 | Nguyen ............... A61K 8/31 424/70.17 |
| 2012/0276037 A1 | 11/2012 | Suzuki et al. |

FOREIGN PATENT DOCUMENTS

| | | | |
|---|---|---|---|
| EP | 0337354 | A1 | 10/1989 |
| FR | 1583363 | A | 10/1969 |
| FR | 2077143 | A5 | 10/1971 |
| FR | 2080759 | A1 | 11/1971 |
| FR | 2162025 | A1 | 7/1973 |
| FR | 2190406 | A2 | 2/1974 |
| FR | 2252840 | A1 | 6/1975 |
| FR | 2270846 | A1 | 12/1975 |
| FR | 2280361 | A2 | 2/1976 |
| FR | 2316271 | A1 | 1/1977 |
| FR | 2320330 | A1 | 4/1977 |
| FR | 2336434 | A1 | 7/1977 |
| FR | 2368508 | A2 | 5/1978 |
| FR | 2383660 | A1 | 10/1978 |
| FR | 2393573 | A1 | 1/1979 |
| FR | 2413907 | A1 | 8/1979 |
| FR | 2470596 | A1 | 6/1981 |
| FR | 2505348 | A1 | 11/1982 |
| FR | 2519863 | A1 | 7/1983 |
| FR | 2542997 | A1 | 9/1984 |
| GB | 1546809 | A | 5/1979 |
| WO | 0006094 | A1 | 2/2000 |
| WO | 0176543 | A1 | 10/2001 |
| WO | 2014/023440 | A1 | 2/2014 |

* cited by examiner

COSMETIC COMPOSITION COMPRISING NON-AMINO POLYALKYLSILOXANES, OXYETHYLENATED POLYMERS AND FATTY ALCOHOLS

CROSS REFERENCE TO RELATED APPLICATIONS

This is a national stage application of PCT/EP2016/057050, filed internationally on Mar. 31, 2016, which claims priority to Indian Application No. 952/DEL/2015, filed on Apr. 2, 2015, both of which are incorporated by reference herein in their entireties.

The present invention relates to a cosmetic composition comprising one or more particular non-amino polyalkylsiloxanes comprising at least one fatty chain, one or more oxyethylenated polymers and one or more fatty alcohols.

The invention also relates to a cosmetic treatment process of keratin materials, and particularly a method for conditioning keratin fibres, and in particular human keratin fibres, using this composition.

Many people are unsatisfied with the way their hair looks, and have difficulty in styling it. Hair is generally damaged and embrittled by the action of external atmospheric agents such as light and bad weather, but also by mechanical or chemical treatments, such as brushing, combing, dyeing, bleaching, permanent-waving and/or relaxing.

Hair is thus damaged by these various factors and may over time become dry, coarse or dull, especially in fragile areas.

Thus, to overcome these drawbacks, it is common practice to use care compositions that condition the hair appropriately, giving it satisfactory cosmetic properties, especially in terms of smoothness, sheen, softness, suppleness, lightness, a natural feel and good disentangling properties.

These hair care compositions may be, for example, conditioning shampoos, hair conditioners, masks or sera, and may be in the form of gels, hair lotions or care creams that are more or less thick. These compositions may be rinsed-out or leave-in compositions.

These compositions generally comprise a combination of cationic conditioning agents such as cationic surfactants, cationic polymers, silicones and/or fatty substances, such as fatty alcohols, in order to give the hair satisfactory cosmetic properties, especially in terms of softness, smoothness and suppleness.

However, such conditioning agents, and in particular fatty alcohols, often have the drawback of making the hair very lank and heavy, which leads to the phenomenon commonly known as the "dull effect". In other words, fatty alcohols become deposited in a large amount on the hair, which has the consequence of making the hair lank, oily and dull.

Nevertheless, removal or reduction of these fatty materials decreases the conditioning effects, and thus the cosmetic properties of the hair.

Most of these compositions also comprise silicones. Indeed, these compounds are known to improve the cosmetic properties of hair, especially in terms of smoothness and flexibility (as shown in JP 48(1973)-19941, JP 56(1986)-92808, and U.S. Pat. No. 5,374,421). However, several disadvantages remain. For instance, hair treated with these compositions remains lank and sticky, and may present a poor combability.

Therefore, there is a real need to develop compositions that do not have the drawbacks described above, i.e. which are able to improve the cosmetic properties of the hair, especially in terms of wet and dry combability, suppleness, smoothness, manageability and shine, without overloading the hair, or leading to a greasy feel or appearance.

The Applicant has now discovered that a cosmetic composition, comprising one or more particular non-amino polyalkylsiloxanes, one or more oxyethylenated polymers in presence of fatty alcohols, makes it possible to achieve the objectives outlined above.

In particular, it has been found that hair treated with such a combination is less lank and heavy while the cosmetic properties are improved. The hair is also easily combed, leading to a better manageability.

Thus, the subject of the invention is a cosmetic composition comprising:
one or more non-amino polyalkylsiloxanes comprising at least one alkyl chain having at least 12 carbon atoms,
one or more oxyethylenated polymers, and
one or more fatty alcohols.

The composition of the present invention is able to improve the cosmetic properties of keratin fibres, in particular human keratin fibres such as the hair, especially in terms of shine, softness, smoothness and suppleness while at same time giving the hair a good wet and dry combability, as well as an improved manageability.

The hair is not overloaded, remains light and has no greasy appearance and feel. The composition is also non sticky on hands with a smooth glide feel on hand.

The invention also relates to a method for conditioning keratin fibres, and in particular human keratin fibres, by applying the cosmetic composition of the invention on said keratin fibres.

Other subjects, characteristics, aspects and advantages of the invention will emerge even more clearly on reading the description and the example that follows.

In the description that follows and unless otherwise indicated, the limits of a range of values are included within this range, in particular in the expressions "of between" and "ranging from . . . to . . . ".

Moreover, the expression "at least one" used in the present description is equivalent to the expression "one or more".

Polyalkylsiloxanes

The cosmetic composition, according to the present invention, comprises one or more non-amino polyalkylsiloxanes comprising at least one alkyl chain having at least 12 carbon atoms.

According to the present invention, the term "non-amino polyalkylsiloxane" denotes any polyalkylsiloxane that does not contain any primary, secondary or tertiary amino group, or a quaternary ammonium group.

The polyalkylsiloxanes, which can be used in the composition according to the invention, may be in the form of oils, waxes, resins or gums.

The non-amino polyalkylsiloxanes suitable for the present invention are preferentially chosen from the compounds of general formula (I)

$$R_2-\underset{\underset{R_3}{|}}{\overset{\overset{R_3}{|}}{Si}}-O-\left[\underset{\underset{R_3}{|}}{\overset{\overset{R_3}{|}}{Si}}-O\right]_n\left[\underset{\underset{R_3}{|}}{\overset{\overset{R_3}{|}}{Si}}-O\right]_m\underset{\underset{R_3}{|}}{\overset{\overset{R_3}{|}}{Si}}-R_2 \quad (I)$$

wherein,
$R_1$ and $R_2$, which may be identical or different, represent a saturated or unsaturated, linear or branched, alkyl radical comprising from 1 to 30 carbon atoms, it being understood that at least one of the groups $R_1$ or $R_2$ comprises at least 12 carbon atoms, preferably from 12 to 22 carbon atoms, and more preferentially from 16 to 18 carbon atoms;

$R_3$ represents a saturated or unsaturated, linear or branched, alkyl radical containing from 1 to 6 carbon atoms; and n and m are integers ranging, independently from each other, from 0 to 2000 and whose sum ranges from 1 to 2000; provided that when $R_2$ comprises less than 12 carbon atoms, m is greater than or equal to 1.

The non-amino polyalkylsiloxanes in the composition of the present invention are preferentially chosen from compounds of formula (I) wherein at least one of the groups $R_1$ or $R_2$ represents a saturated, linear alkyl radical comprising from 12 to 22 carbon atoms, and better still from 16 to 18 carbon atoms, and $R_3$ represents a saturated, linear alkyl radical comprising from 1 to 4 carbon atoms.

Preferably, according to a first embodiment, $R_1$ represents a saturated, linear alkyl radical comprising at least 12 carbon atoms, more preferentially from 12 to 22 carbon atoms, better still from 16 to 18 carbon atoms, and $R_2$ represents a saturated linear alkyl radical comprising from 1 to 4 carbon atoms, and more preferentially a methyl group.

Preferably, in a second embodiment, $R_2$ represents a saturated, linear alkyl radical comprising at least 12 carbon atoms, more preferentially from 12 to 22 carbon atoms, better still from 16 to 18 carbon atoms, and $R_1$ represents a saturated linear alkyl radical comprising from 1 to 4 carbon atoms, and more preferentially a methyl group.

Preferably, $R_3$ represents a saturated, linear alkyl radical comprising from 1 to 4 carbon atoms, and more preferentially $R_3$ represents a methyl group.

Furthermore, the weight-average molecular mass (Mw) of the non-amino polyalkylsiloxane preferably ranges from 2000 to $10^6$, and more preferentially from 10 000 to 800 000.

More particularly, n ranges from 0 to 999 and m ranges from 1 to 1000, the sum of n and m ranging from 1 to 1000.

Preferably, the sum of n and m ranges from 5 to 800, and more preferentially from 50 to 750.

The non-amino polyalkylsiloxanes preferentially used in the present invention are chosen from polyalkylmethylsiloxanes comprising at least one alkyl chain having at least 12 carbon atoms, more preferentially from 12 to 22 carbon atoms, better still from 16 to 18 carbon atoms, and even more particularly chosen from cetyl dimethicone, stearyl dimethicone and mixtures thereof.

Such compounds are for example the commercial products Abil Wax 9801 (Evonik Goldschmidt) or Dow Corning 2502 cosmetic fluid (Dow Corning).

The amount of non-amino polyalkylsiloxanes comprising an alkyl chain of at least 12 carbon atoms, in the composition of the present invention, advantageously ranges from 0.05 to 15% by weight, and more preferentially from 0.1 to 10% by weight, relative to the total weight of the composition.

Oxyethylenated Polymers

The cosmetic composition, according to the present invention, further comprises one or more oxyethylenated polymers.

The oxyethylenated polymers that may be used in the composition of the invention have preferably a weight-average molecular mass greater than or equal to $10^6$. More preferentially, the weight-average molecular mass ranges from $10^6$ to $6*10^6$, and better still from $1.5*10^6$ to $4*10^6$.

According to the present invention, an oxyethylenated polymer means a polymer comprising at least one oxyethylenated unit.

According to one preferred embodiment of the invention, the oxyethylenated polymers are chosen from the compounds of general formula (II)

$$H(OCH_2CH_2)_zOH \qquad (II)$$

wherein, z is an integer greater than or equal to 30 000, preferably z ranges from 30 000 to 120 000, and more preferentially from 40 000 to 95 000.

As oxyethylenated polymer preferably used in the composition of the invention, mention may be made especially of PEG-45M (formula (II) wherein z is 45 000) such as the product sold under the name Polyox WSR N 60 K by the company Amerchol, and of PEG-90M (formula (II) wherein z is 90 000), and mixtures thereof.

The amount of oxyethylenated polymers, in the composition of the present invention, advantageously ranges from 0.001 to 1% by weight, and more preferentially from 0.001 to 0.5% by weight, relative to the total weight of the composition.

Fatty Alcohols

The cosmetic composition, according to the present invention, further comprises one or more fatty alcohols.

For the purposes of the present invention, the term "fatty alcohol" means any saturated or unsaturated, linear or branched alcohol comprising at least 8 carbon atoms and which is not oxyalkylenated.

Preferably, the fatty alcohols are solid at room temperature (25° C.) and at atmospheric pressure (1.013*$10^5$Pa). The fatty alcohols are preferably chosen from the compounds of general formula (III)

$$R\text{—}OH \qquad (III)$$

wherein R denotes a saturated or unsaturated, linear or branched radical containing from 8 to 30, preferably from 10 to 30 carbon atoms, more preferentially from 12 to 22 carbon atoms, and better still from 16 to 22 carbon atoms.

R preferably denotes a linear or branched $C_8$-$C_{30}$, more preferentially $C_{16}$-$C_{22}$ alkyl or a linear or branched $C_8$-$C_{30}$, more preferentially $C_{16}$-$C_{22}$ alkenyl group, and better still linear. R may be substituted with one or more hydroxyl groups.

Examples of fatty alcohols that may be mentioned include cetyl alcohol, stearyl alcohol, oleyl alcohol, behenyl alcohol, linoleyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

Fatty alcohol mixtures that may be mentioned include cetylstearyl (or cetearyl) alcohol.

Among all the fatty alcohols that may be used according to the invention, use is preferably made of one or more fatty alcohols chosen from cetyl alcohol, stearyl alcohol, and mixtures thereof such as cetearyl alcohol.

The amount of fatty alcohols, in the composition of the present invention, advantageously ranges from 0.05 to 15% by weight, preferably from 0.1 to 10% by weight, and more preferentially from 0.5 to 7% by weight, relative to the total weight of the composition.

Conditioning Agents

The cosmetic composition, according to the present invention, may further comprise one or more conditioning agents, chosen from cationic surfactants, cationic polymers and mixtures thereof.

Cationic Surfactants

The cosmetic composition may comprise one or more cationic surfactants.

The term "cationic surfactant" means a surfactant that is positively charged when it is contained in the composition according to the invention. This surfactant may bear one or more positive permanent charges or may contain one or more cationizable functions in the composition according to the invention.

The cationic surfactants are preferably chosen from primary, secondary or tertiary fatty amines, optionally polyoxyalkylenated, or salts thereof, and quaternary ammonium salts, and mixtures thereof.

The fatty amines generally comprise at least one $C_8$-$C_{30}$ hydrocarbon-based chain, and preferably a $C_{12}$-$C_{22}$ alkyl chain.

As example of fatty amines, mention may be made of stearamidopropyl dimethylamine.

Examples of quaternary ammonium salts that may especially be mentioned include:

quaternary ammonium salts of general formula (IV)

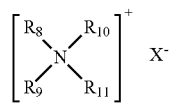
(IV)

wherein, $R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 12 to 22 carbon atoms, and preferably from 16 to 22 carbon atoms; and $X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)alkylaryl sulfonates.

The aliphatic groups may comprise heteroatoms especially such as oxygen, nitrogen, sulfur and halogens. The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, acetates, phosphates, lactates, ($C_1$-$C_4$)alkyl sulfates, and ($C_1$-$C_4$)alkyl- or ($C_1$-$C_4$) alkylarylsulfonates.

Among the quaternary ammonium salts of formula (IV), those that are preferred are, on the one hand, tetraalkylammonium salts, for instance dialkyldimethylammonium or alkyltrimethylammonium salts in which the alkyl group contains approximately from 16 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds.

quaternary ammonium salts of imidazoline, for instance, those of formula (V)

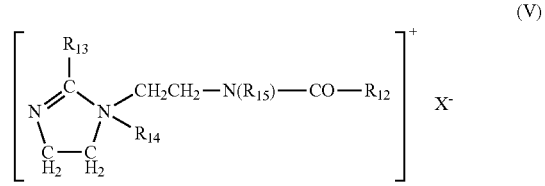
(V)

wherein, $R_{12}$ represents an alkyl or alkenyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group; $X^-$ is an anion chosen from the group of halides, phosphates, acetates, lactates, alkyl sulfates, alkyl- or alkylarylsulfonates in which the alkyl and aryl groups each preferably comprise from 1 to 20 carbon atoms and from 6 to 30 carbon atoms.

$R_{12}$ and $R_{13}$ preferably denote a mixture of alkyl or alkenyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

di- or tri-quaternary ammonium salts, in particular of formula (VI)

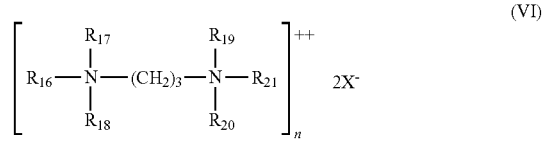
(VI)

wherein, $R_{16}$ denotes an alkyl radical comprising approximately from 16 to 30 carbon atoms which is optionally hydroxylated and/or interrupted by one or more oxygen atoms, $R_{17}$ is chosen from hydrogen and an alkyl radical comprising from 1 to 4 carbon atoms and an $(R_{16a})(R_{17a})(R_{18a})N$—$(CH_2)_3$ group, $R_{16a}$, $R_{17a}$, $R_{18a}$, $R_{18}$, $R_{19}$, $R_{20}$ and $R_{21}$, which may be identical or different, are chosen from hydrogen and an alkyl radical comprising from 1 to 4 carbon atoms and $X^-$ is an anion chosen from the group of halides, acetates, phosphates, nitrates and methyl sulfates.

Such compounds are, for example, Finquat CT-P, available from the company Finetex (Quaternium 89), and Finquat CT, available from the company Finetex (Quaternium 75), quaternary ammonium salts containing at least one ester function, such as those of formula (VII)

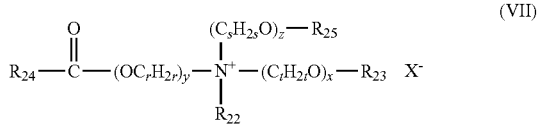
(VII)

wherein, $R_{22}$ is chosen from $C_1$-$C_6$ alkyl groups and $C_1$-$C_6$ hydroxyalkyl or dihydroxyalkyl groups;

$R_{23}$ is chosen from:

the group

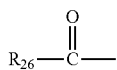

groups R$_{27}$, which are linear or branched, saturated or unsaturated C$_1$-C$_{22}$ hydrocarbon-based groups,
a hydrogen atom,
R$_{25}$ is chosen from:
the group

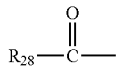

groups R$_{29}$, which are linear or branched, saturated or unsaturated C$_1$-C$_6$ hydrocarbon-based groups,
a hydrogen atom,
R$_{24}$, R$_{26}$ and R$_{28}$, which may be identical or different, are chosen from linear or branched, saturated or unsaturated C$_7$-C$_{21}$ hydrocarbon-based groups;
r, s and t, which may be identical or different, are integers ranging from 2 to 6;
y is an integer ranging from 1 to 10;
x and z, which may be identical or different, are integers ranging from 0 to 10;
X$^-$ is a simple or complex, organic or mineral anion;
with the proviso that the sum x+y+z is from 1 to 15, that when x is 0 then R$_{23}$ denotes R$_{27}$, and that when z is 0 then R$_{25}$ denotes R$_{29}$.

The alkyl groups R$_{22}$ may be linear or branched, and more particularly linear.

Preferably, R$_{22}$ denotes a methyl, ethyl, hydroxyethyl or dihydroxypropyl group, and more particularly a methyl or ethyl group.

Advantageously, the sum x+y+z is from 1 to 10.

When R$_{23}$ is an R$_{27}$ hydrocarbon-based group, it may be long and may contain from 12 to 22 carbon atoms, or may be short and may have from 1 to 3 carbon atoms.

When R$_{25}$ is an R$_{29}$ hydrocarbon-based group, it preferably contains 1 to 3 carbon atoms.

Advantageously, R$_{24}$, R$_{26}$ and R$_{28}$, which may be identical or different, are chosen from linear or branched, saturated or unsaturated C$_{11}$-C$_{21}$ hydrocarbon-based groups, and more particularly from linear or branched, saturated or unsaturated C$_{11}$-C$_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion X$^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion X$^-$ is even more particularly chloride or methyl sulfate.

Use is made more particularly in the composition according to the invention of the ammonium salts of formula (VII) wherein:
R$_{22}$ denotes a methyl or ethyl group;
x and y are equal to 1;
z is equal to 0 or 1;
r, s and t are equal to 2;
R$_{23}$ is chosen from:
the group

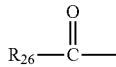

methyl, ethyl or C$_{14}$-C$_{22}$ hydrocarbon-based groups;
a hydrogen atom;
R$_{25}$ is chosen from:
the group

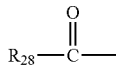

a hydrogen atom;
R$_{24}$, R$_{26}$ and R$_{28}$, which may be identical or different, are chosen from linear or branched, saturated or unsaturated C$_{13}$-C$_{17}$ hydrocarbon-based groups, and preferably from linear or branched, saturated or unsaturated C$_{13}$-C$_{17}$ alkyl and alkenyl groups.

The hydrocarbon-based groups are advantageously linear.

Mention may be made, for example, of the compounds of formula (VII) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with C$_{10}$-C$_{30}$ fatty acids or with mixtures of C$_{10}$-C$_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may be made of behenoylhydroxypropyltrimethylammonium chloride, provided by Kao under the name Quatarmin BTC 131.

Preferably, the ammonium salts containing at least one ester function contain two ester functions.

Among the quaternary ammonium salts containing at least one ester function, which may be used, it is preferred to use dipalmitoylethylhydroxyethylmethylammonium salts.

Cationic Polymers

The cosmetic composition may comprise one or more cationic polymers.

The term "cationic polymer" means any polymer containing cationic groups and/or groups that can be ionized to cationic groups, which are preferably non-siliceous.

The cationic polymers that may be used in accordance with the present invention may be chosen from any of those already known per se for styling the hair, namely, especially, those described in patent application EP-A-0 337 354 and in French patent applications FR-A-2 270 846, 2 383 660, 2 598 611, 2 470 596 and 2 519 863.

The preferred cationic polymers that may be used in the composition according to the invention are chosen from those containing units comprising primary, secondary, tertiary and/or quaternary amine groups that may either form part of the main polymer chain or may be borne by a side substituent directly connected thereto.

The cationic polymers preferably have a weight-average molecular mass of greater than $10^5$, preferably greater than $10^6$ and more preferably of between $10^6$ and $10^8$.

Among the cationic polymers that may be used in accordance with the invention, mention may be made more particularly of polymers of polyamine, polyaminoamide and polyquaternary ammonium type.

The polymers of polyamine, polyaminoamide and polyquaternary ammonium type that may be used in the composition according to the present invention are especially those described in French patents 2 505 348 and 2 542 997.

Among these polymers, mention may be made especially of:

(1) homopolymers or copolymers derived from acrylic or methacrylic esters or amides and comprising at least one of the units of formulae (VIII), (IX), (X) and (XI) below:

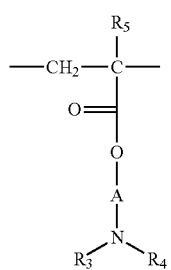

(VIII)

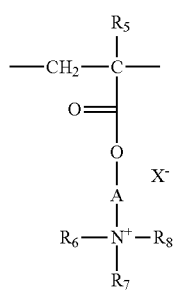

(IX)

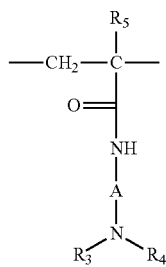

(X)

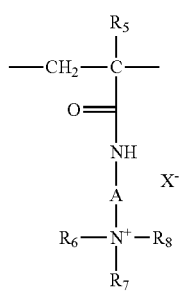

(XI)

wherein,
$R_3$ and $R_4$, which may be identical or different, represent a hydrogen atom or an alkyl group containing from 1 to 6 carbon atoms, and preferably a methyl or ethyl group,
$R_5$, which may be identical or different, denote a hydrogen atom or a $CH_3$ group,
A, which may be identical or different, represent a linear or branched alkyl group of 1 to 6 carbon atoms, preferably 2 or 3 carbon atoms, or a hydroxyalkyl group comprising 1 to 4 carbon atoms,
$R_6$, $R_7$ and $R_8$, which may be identical or different, represent an alkyl group containing from 1 to 18 carbon atoms or a benzyl group, and preferably an alkyl group containing from 1 to 6 carbon atoms, and
$X^-$ denotes an anion derived from a mineral or organic acid, preferably a methosulfate anion or a halide, and better still a chloride or bromide.

The copolymers of family (1) may also contain one or more units derived from comonomers which may be chosen from the family of acrylamides, methacrylamides, diacetone acrylamides, acrylamides and methacrylamides substituted on the nitrogen atom with lower ($C_1$-$C_4$)alkyls, acrylic or methacrylic acids or esters thereof, vinyllactams such as vinylpyrrolidone or vinylcaprolactam, and vinyl esters.

Thus, among these copolymers of the family (1), mention may be made of:
copolymers of acrylamide and of dimethylaminoethyl methacrylate quaternized with dimethyl sulfate or with a dimethyl halide, such as the product sold under the name Hercofloc by the company Hercules,
copolymers of acrylamide and of methacryloyloxyethyltrimethylammonium chloride, described, for example, in patent application EP-A-080 976 and sold under the name Bina Quat P 100 by Ciba-Geigy,
the copolymer of acrylamide and of methacryloyloxyethyltrimethylammonium methosulfate sold under the name Reten by the company Hercules,
quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylamino ethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and crosslinked polymers of methacryloyloxy($C_1$-$C_4$)alkyltri ($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion containing 50% by weight of the said copolymer in mineral oil. This dispersion is sold under the name Salcare® SC 92 by the company Ciba. Use may also be made of a crosslinked methacryloyloxyethyltrimethylammonium chloride homopolymer (INCI name Polyquaternium-37), for example the polymer sold under the name Cosmedia Ultragel 300 by the company Cognis; or as a dispersion in mineral oil or in a liquid ester; these dispersions are sold under the names Salcare® SC 95 and Salcare® SC 96 by the company Ciba.

(2) polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are especially described in French patents 2 162 025 and 2 280 361.

(3) water-soluble polyamino amides prepared in particular by polycondensation of an acidic compound with a polyamine. These polyaminoamides may be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide. These polyaminoamides can be alkylated or, if they comprise one or more tertiary amine functions, they can be quaternized. Such polymers are especially described in French patents 2 252 840 and 2 368 508.

(4) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group comprises from 1 to 4 carbon atoms and preferably denotes methyl, ethyl or propyl. Such polymers are especially described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The mole ratio between the polyalkylene polyamine and the dicarboxylic acid is between 0.8:1 and 1.4:1; the polyamino amide resulting therefrom is reacted with epichlorohydrin in a mole ratio of epichlorohydrin relative to the secondary amine group of the polyamino amide of between 0.5:1 and 1.8:1. Such polymers are described in particular in U.S. Pat. No. 3,227,615 and 2 961 347.

Polymers of this type are sold in particular under the name Hercosett 57 by the company Hercules Inc. or alternatively under the name PD 170 or Delsette 101 by the company Hercules in the case of the adipic acid/epoxypropyl-diethylenetriamine copolymer.

(6) Cyclopolymers of alkyldiallylamine or of dialkyldiallylammonium, such as the homopolymers or copolymers comprising, as main constituent of the chain, units corresponding to formula (XII) or (XIII):

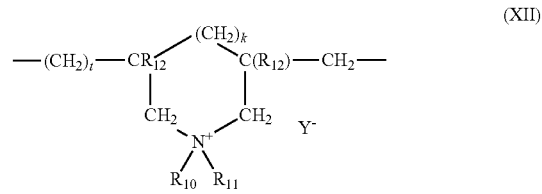

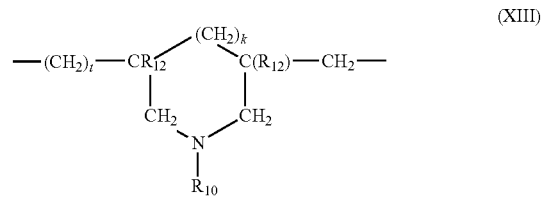

wherein, k and t are equal to 0 or 1, the sum k+t being equal to 1; $R_{12}$ denotes a hydrogen atom or a methyl group; $R_{10}$ and $R_{11}$, independently of each other, denote an alkyl group containing from 1 to 6 carbon atoms, a hydroxyalkyl group in which the alkyl group preferably contains 1 to 5 carbon atoms, a lower ($C_1$-$C_4$) amidoalkyl group, or $R_{10}$ and $R_{11}$ may denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

$R_{10}$ and $R_{11}$, independently of each other, preferably denote an alkyl group having from 1 to 4 carbon atoms.

Among the polymers defined above, mention may be made more particularly of the dimethyldiallylammonium chloride homopolymer sold under the name Merquat 100 by the company Nalco and its homologues of low weight-average molecular weights, and the copolymers of diallyldimethylammonium chloride and of acrylamide sold under the name Merquat 550.

(7) The quaternary diammonium polymer in particular containing repeating units corresponding to the formula (XIV):

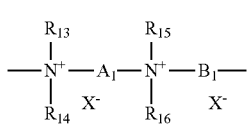 (XIV)

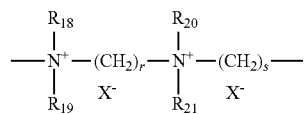 (XV)

wherein,
$R_{13}$, $R_{14}$, $R_{15}$ and $R_{16}$, which may be identical or different, represent aliphatic, alicyclic or arylaliphatic groups containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl group substituted with a nitrile, ester, acyl or amide group or a group $COOR_{17}D$ or $CONHR_{17}D$ where $R_{17}$ is an alkylene and D is a quaternary ammonium group, $A_1$ and $B_1$ represent polymethylene groups containing from 2 to 20 carbon atoms which may be linear or branched, and saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid.

$A_1$, $R_{13}$ and $R_{15}$ can form, with the two nitrogen atoms to which they are attached, a piperazine ring.

In addition, if $A_1$ denotes a linear or branched, saturated or unsaturated alkylene or hydroxyalkylene radical, $B_1$ may also denote a group $(CH_2)_n$—CO-D-OC—$(CH_2)_p$—, n and p are integers ranging from 2 to 20 approximately, in which D denotes:

a) a glycol residue of formula: —O—Z—O—, where Z denotes a linear or branched hydrocarbon-based radical or a group corresponding to one of the following formulae:

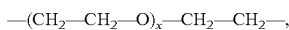

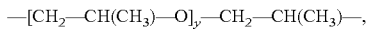

in which x and y denote an integer from 1 to 4, representing a defined and unique degree of polymerization or any number from 1 to 4 representing an average degree of polymerization, b) a bis-secondary diamine residue such as a piperazine derivative, c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_{2-5}$ d) a ureylene group of formula —NH—CO—NH—.

Preferably, $X^-$ is an anion such as chloride or bromide.

These polymers have a number-average molecular mass generally of between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (XV):

wherein, $R_{18}$, $R_{19}$, $R_{20}$ and $R_{21}$, which may be identical or different, denote an alkyl or hydroxyalkyl group containing from 1 to 4 carbon atoms approximately, r and s are integers ranging from 2 to 20 approximately, and $X^-$ is an anion derived from a mineral or organic acid.

A compound of formula (XV) that is particularly preferred is that for which $R_{18}$, $R_{19}$, $R_{20}$ and $R_{21}$ represent a methyl radical and r=3, s=6 and X=Cl, called hexadimethrine chloride in INCI nomenclature (CTFA).

(8) Polyquaternary ammonium polymers formed especially from units of formula (XVI):

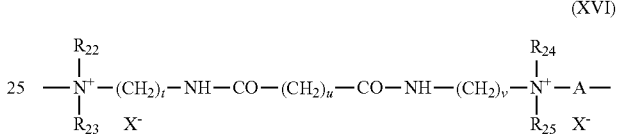 (XVI)

wherein,
$R_{22}$, $R_{23}$, $R_{24}$ and $R_{25}$, which may be identical or different, represent a hydrogen atom or a methyl, ethyl, propyl, β-hydroxyethyl, β-hydroxypropyl or —$CH_2CH_2$($OCH_2CH_2$)$_p$OH group, where p is equal to 0 or to an integer between 1 and 6, with the proviso that $R_{22}$, $R_{23}$, $R_{24}$ and $R_{25}$ do not simultaneously represent a hydrogen atom, t and u, which may be identical or different, are integers between 1 and 6, v is equal to 0 or to an integer between 1 and 34, $X^-$ denotes an anion such as a halide, and A denotes a dihalide radical or preferably represents —$CH_2$—$CH_2$—O—$CH_2$—$CH_2$—.

Such compounds are especially described in patent application EP-A-122 324.

Among these, mention may be made, for example, of the products Mirapol® A 15, Mirapol® AD1, Mirapol® AZ1 and Mirapol® 175, sold by the company Miranol.

(9) Quaternary polymers of vinylpyrrolidone and/or of vinylimidazole, for instance the products sold under the names Luviquat® FC 905, FC 550 and FC 370 and Luviquat Excellence by the company BASF.

(10) Cationic polysaccharides, preferably cationic celluloses and galactomannan gums.

Among cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are described in French patent 1 492 597. These polymers are also defined in the CTFA dictionary as quaternary ammoniums of hydroxyethylcellulose that have reacted with an epoxide substituted with a trimethylammonium group.

The cationic cellulose copolymers or the cellulose derivatives grafted with a water-soluble quaternary ammonium monomer are described especially in U.S. Pat. No. 4,131,576, such as hydroxyalkyl celluloses, for instance hydroxymethyl, hydroxyethyl or hydroxypropyl celluloses grafted especially with a methacryloylethyltrimethylammonium, methacrylamidopropyltrimethylammonium or dimethyldiallylammonium salt.

A cationic cellulose copolymer that may especially be mentioned is Polyquaternium-4, which is a copolymer of hydroxyethylcellulose and of diallyldimethylammonium chloride.

Mention may also be made of associative celluloses such as alkylhydroxyethylcelluloses quaternized with $C_8$-$C_{30}$ fatty chains, such as the product Quatrisoft LM 200®, sold by the company Amerchol/Dow Chemical (INCI name Polyquaternium-24) and the products Crodacel QM® (INCI name PG-Hydroxyethylcellulose cocodimonium chloride), Crodacel QL® ($C_{12}$ alkyl) (INCI name PG-Hydroxyethylcellulose lauryldimonium chloride) and Crodacel QS® ($C_{18}$ alkyl) (INCI name PG-Hydroxyethylcellulose stearyldimonium chloride) sold by the company Croda.

Mention may also be made of other fatty-chain hydroxyethylcellulose derivatives such as the commercial products Softcat Polymer SL® such as SL-100, SL-60, SL-30 and SL-5 from the company Amerchol/Dow chemical of INCI name Polyquaternium-67.

The cationic galactomannan gums are described more particularly in U.S. Pat. No. 3,589,578 and 4 031 307, in particular guar gums containing cationic trialkylammonium groups. Guar gums modified with a salt such as 2,3-epoxypropyltrimethylammonium chloride are used, for example.

(11) Cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

The cationic proteins or protein hydrolysates are, in particular, chemically modified polypeptides bearing quaternary ammonium groups at the end of the chain, or grafted thereon. Their molecular mass may vary, for example, from 1500 to 10 000 and in particular from 2000 to 5000 approximately. Among these compounds, mention may be made especially of:

collagen hydrolysates bearing triethylammonium groups, such as the products sold under the name Quat-Pro E by the company Maybrook and referred to in the CTFA dictionary as Triethonium Hydrolyzed Collagen Ethosulfate, collagen hydrolysates bearing trimethylammonium chloride and trimethylstearylammonium chloride groups, which are sold under the name Quat-Pro S by the company Maybrook and are referred to in the CTFA dictionary as Steartrimonium Hydrolyzed Collagen, animal protein hydrolysates bearing trimethylbenzylammonium groups, such as the products sold under the name Crotein BTA by the company Croda and referred to in the CTFA dictionary as Benzyltrimonium hydrolyzed animal protein, protein hydrolysates bearing quaternary ammonium groups on the polypeptide chain, the said ammonium groups comprising at least one alkyl radical having from 1 to 18 carbon atoms.

Among these protein hydrolysates, mention may be made, inter alia, of:

Croquat L, in which the quaternary ammonium groups comprise a $C_{12}$ alkyl group, Croquat M, in which the quaternary ammonium groups comprise $C_{10}$-$C_{18}$ alkyl groups, Croquat S, in which the quaternary ammonium groups comprise a $C_{18}$ alkyl group, Crotein Q, in which the quaternary ammonium groups comprise at least one alkyl group having from 1 to 18 carbon atoms.

These various products are sold by the company Croda.

Other quaternized proteins or hydrolysates are, for example, those corresponding to the formula (XVII):

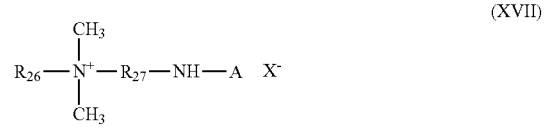

wherein, $X^-$ is an anion of an organic or mineral acid, A denotes a protein residue derived from collagen protein hydrolysates, $R_{26}$ denotes a lipophilic group comprising up to 30 carbon atoms, $R_{27}$ represents an alkylene group having 1 to 6 carbon atoms. Mention may be made, for example, of the products sold by the company Inolex, under the name Lexein QX 3000, referred to in the CTFA dictionary as Cocotrimonium Collagen Hydrolysate.

Mention may also be made of quaternized plant proteins such as wheat, corn or soybean proteins, for instance quaternized wheat proteins. Mention may be made of those sold by the company Croda under the names Hydrotriticum WQ or QM, referred to in the CTFA dictionary as Cocodimonium hydrolysed wheat protein, Hydrotriticum QL, referred to in the CTFA dictionary as Laurdimonium hydrolysed wheat protein, or else Hydrotriticum QS, referred to in the CTFA dictionary as Steardimonium hydrolysed wheat protein.

(12) Polyamines such as Polyquart R H sold by Cognis, referred to under the name polyethylene glycol (15) tallow polyamine in the CTFA dictionary.

(13) Polymers comprising in their structure:

(a) one or more units corresponding to formula (A) below:

(b) optionally one or more units corresponding to formula (B) below:

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide.

This hydrolysis may be performed in an acidic or basic medium.

The weight-average molecular mass of the said polymer, measured by light scattering, may range from 1000 to 3 000 000 g/mol, preferably from 10 000 to 1 000 000 g/mol and more particularly from 100 000 to 500 000 g/mol.

The cationic charge density of these polymers can vary from 2 to 20 meq/g, preferably from 2.5 to 15 meq/g and more particularly from 3.5 to 10 meq/g.

The polymers comprising units of formula (A) and optionally units of formula (B) are sold especially under the name Lupamin by the company BASF, for instance, and in a non-limiting manner, the products sold under the names Lupamin 9095, Lupamin 5095, Lupamin 1095, Lupamin 9030 and Lupamin 9010.

Preferably, the conditioning agents, in the composition of the present invention, are chosen from cationic surfactants, and more preferentially from tertiary fatty amines comprising a $C_{12}$-$C_{22}$ alkyl chain, quaternary ammonium salts of general formula (IV) and mixtures thereof.

Better still, the conditioning agents suitable for the present invention are chosen from stearamidopropyl dimethylamine, behentrimonium chloride, cetrimonium chloride and mixtures thereof.

When they are present, the amount of conditioning agents as described above, in the composition of the present invention, advantageously ranges from 0.01 to 10% by weight, and more preferentially from 0.05 to 5% by weight, relative to the total weight of the composition.

Liquid Fatty Substances

The cosmetic composition, according to the present invention, may further comprise one or more fatty substances that are liquid at room temperature (25° C.) and at atmospheric pressure ($1.013*10^5$Pa), different from the fatty alcohols described above.

The term "fatty substance" means an organic compound that is insoluble in water at ordinary temperature (25° C.) and at atmospheric pressure ($1.013*10^5$Pa) (solubility of less than 5%, preferably of less than 1% and even more preferentially of less than 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

In addition, the liquid fatty substances of the present invention are nonpolyoxyethylenated and nonpolyglycerolated.

The term "oil" means a "fatty substance" that is liquid at room temperature (25° C.) and at atmospheric pressure ($1.013*10^5$Pa).

The term "non-silicone oil" means an oil not containing any silicon atoms (Si) and the term "silicone oil" means an oil containing at least one silicon atom.

More particularly, the liquid fatty substances can be chosen from non-silicone oils such as in particular $C_6$-$C_{16}$ liquid hydrocarbons, liquid hydrocarbons containing more than 16 carbon atoms, non-silicone oils of animal origin, triglycerides of plant or synthetic origin, fluoro oils, liquid fatty acid and/or fatty alcohol esters other than triglycerides, and mixtures thereof.

It is recalled that the fatty esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds can comprise one to three conjugated or nonconjugated carbon-carbon double bonds.

As regards the $C_6$-$C_{16}$ liquid hydrocarbons, they are more particularly linear, branched or optionally cyclic, and are preferably alkanes. Examples that may be mentioned include hexane, cyclohexane, undecane, dodecane, tridecane or isoparaffins, such as isohexadecane, isodecane or isododecane, and mixtures thereof.

The linear or branched liquid hydrocarbons of mineral or synthetic origin containing more than 16 carbon atoms are preferably chosen from liquid paraffins, petroleum jelly, liquid petroleum jelly, mineral oil, polydecenes and hydrogenated polyisobutene such as Parleam®, and mixtures thereof.

By way of hydrocarbon-based oils of animal origin, mention may be made of perhydrosqualene.

The triglycerides of vegetable or synthetic origin are preferably chosen from liquid fatty acid triglycerides comprising from 6 to 30 carbon atoms, for instance heptanoic or octanoic acid triglycerides, or alternatively, more particularly from those present in plant oils, for instance coconut oil, sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

As regards the liquid fatty acid and/or fatty alcohol esters advantageously other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds can comprise one to three conjugated or non-conjugated carbon-carbon double bonds.

The esters according to this variant can also be chosen from mono-, di-, tri- and tetraesters, polyesters and mixtures thereof.

These esters may be, for example, oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleopalmitate, -linoleate, -linolenate or -oleostearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose mono laurate;
  the products sold under the name Ryoto Sugar Esters, for example referenced B370 and corresponding to sucrose behenate formed from 20% monoester and 80% diester-triester-polyester;
  the sucrose mono-dipalmitate/stearate sold by the company Goldschmidt under the name Tegosoft® PSE.

The liquid fatty substances present in the composition can also be chosen from silicone oils different from the non-amino polyalkylsiloxanes comprising at least one alkyl chain having at least 12 carbon atoms.

The silicones oils that may be used in the composition of the present invention are volatile or non-volatile, cyclic, linear or branched silicones, which are unmodified or modified by organic groups, having a viscosity from $5*10^{-6}$ to 2.5 $m^2/s$ at 25° C., and preferably $1*10^{-5}$ to 1 $m^2/s$.

Preferably, the silicone oils are chosen from polydialkylsiloxanes different from the non-amino polyalkylsiloxanes comprising at least one alkyl chain having at least 12 carbon atoms, in particular polydimethylsiloxanes (PDMSs), that do not comprise any alkyl chain having at least 12 carbon atoms, and organomodified polysiloxanes comprising at least one functional group chosen from amino groups, aryl groups and alkoxy groups.

Organopolysiloxanes are defined in greater detail in Walter Noll's Chemistry and Technology of Silicones (1968), Academic Press. They may be volatile or non-volatile.

When they are volatile, the silicone oils are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

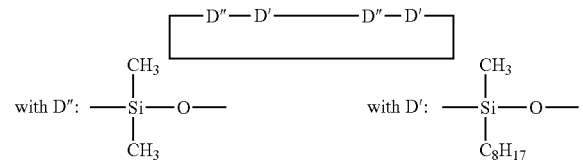

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ $m^2/s$ at 25° C. An example is decamethyltetrasiloxane sold in particular under the name SH 200 by the company Toray Silicone. Silicones coming within this category are also described in the paper published in Cosmetics and Toiletries, Vol. 91, January 76, pp. 27-32, Todd & Byers, "Volatile Silicone Fluids for Cosmetics".

Use is preferably made of non-volatile polydialkylsiloxanes that do not comprise any alkyl chain having at least 12 carbon atoms.

These silicone oils are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without implied limitation, of the following commercial products:
  the Silbione® oils of the 47 and 70 047 series or the Mirasil® oils sold by Rhodia, such as, for example, the oil 70 047 V 500 000;

the oils of the Mirasil® series sold by Rhodia;
the oils of the 200 series from the company Dow Corning, such as DC200 with a viscosity of 60 000 mm$^2$/s;
the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of series 48 from the company Rhodia.

The organomodified silicones that can be used in accordance with the invention are silicones as defined above and comprising in their structure one or more organofunctional group(s) attached via a hydrocarbon-based group.

The organomodified silicone oils may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Mention may also be made, among the organomodified silicones, of polyorganosiloxanes comprising:
substituted or unsubstituted amino groups, such as the products sold under the names GP 4 Silicone Fluid and GP 7100 by Genesee or the products sold under the names Q2 8220 and Dow Corning 929 or 939 by the company Dow Corning. The substituted amino groups are, in particular, $C_1$-$C_4$ aminoalkyl groups;
alkoxylated groups,
hydoxylated groups.

Preferably, the fatty substances, liquid at room temperature (25° C.) and at atmospheric pressure (1.013*10$^5$Pa), different from the fatty alcohols, are chosen from liquid hydrocarbons of mineral or synthetic origin containing more than 16 carbon atoms, triglycerides of plant origin and mixtures thereof, and more preferentially from mineral oil, coconut oil and mixtures thereof.

When they are present, the amount of the liquid fatty substances, different from the fatty alcohols, advantageously ranges from 0.05 to 15% by weight, and more preferentially from 0.1 to 10% by weight, relative to the total weight of the composition.

Additional Surfactants

The cosmetic composition, according to the present invention, may further comprise one or more additional surfactants different from the cationic surfactants described above.

The additional surfactants can be chosen from anionic surfactants, amphoteric or zwitterionic surfactants, nonionic surfactants and mixtures thereof.

The term "anionic surfactant" means a surfactant comprising, as ionic or ionizable groups, only anionic groups.

These anionic groups are preferably chosen from the groups $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, POH and PO$^-$.

As examples of anionic surfactants that may be used in the composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfo succinates, alkylsulfoacetates, acylsarcosinates, acylglutamates, alkylsulfosuccinamates, acylisethionates and N—($C_1$-$C_4$)alkyl N-acyltaurates, salts of alkyl monoesters and of polyglycoside-polycarboxylic acids, acyllactylates, D-galactoside uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds (unless otherwise mentioned) generally comprising from 6 to 24 carbon atoms and the aryl group generally denoting a phenyl group.

These compounds can be oxyethylenated and then preferably comprise from 1 to 50 ethylene oxide units.

The salts of $C_6$-$C_{24}$ alkyl monoesters and of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactants are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, in particular the sodium or magnesium salts.

The anionic surfactants that may be present may be mild anionic surfactants, i.e. anionic surfactants without a sulfate function.

Mention may in particular be made, as regards the mild anionic surfactants, of the following compounds and salts thereof, and also mixtures thereof:
polyoxyalkylenated alkyl ether carboxylic acids;
polyoxyalkylenated alkylaryl ether carboxylic acids;
polyoxyalkylenated alkylamido ether carboxylic acids, in particular those comprising 2 to 50 ethylene oxide groups;
alkyl-D-galactoside uronic acids;
acylsarcosinates, acylglutamates; and
alkylpolyglycoside carboxylic esters.

Use may be made most particularly of polyoxyalkylenated alkyl ether carboxylic acids, for instance lauryl ether carboxylic acid (4.5 OE) sold, for example, under the name Akypo RLM 45 CA from Kao.

The amphoteric or zwitterionic surfactant(s) that may be present in the composition of the present invention may especially be secondary or tertiary aliphatic amine derivatives, optionally quaternized, in which the aliphatic group is a linear or branched chain containing from 8 to 22 carbon atoms, the said amine derivatives containing at least one anionic group, for instance a carboxylate, sulfonate, sulfate, phosphate or phosphonate group.

Mention may be made in particular of $(C_8$-$C_{20})$alkylbetaines, sulfobetaines, $(C_8$-$C_{20})$alkylamido$(C_3$-$C_8)$alkylbetaines or $(C_8$-$C_{20})$alkylamido$(C_6$-$C_8)$alkylsulfobetaines.

Among the secondary or tertiary aliphatic amine derivatives, optionally quaternized, that may be used, as defined above, mention may also be made of the compounds of respective structures ($A_1$), ($A_2$) and ($A_3$) below:

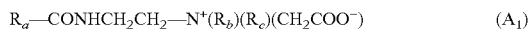

(A$_1$)

wherein,
$R_a$ represents a $C_{10}$-$C_{30}$ alkyl or alkenyl group derived from an acid $R_a$—COOH preferably present in hydrolysed coconut oil, or a heptyl, nonyl or undecyl group,
$R_b$ represents a β-hydroxyethyl group, and
$R_c$ represents a carboxymethyl group;
and

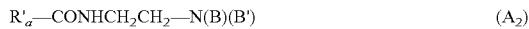

(A$_2$)

wherein,
B represents —CH$_2$CH$_2$OX',
B' represents —(CH$_2$)$_z$—Y', with z=1 or 2,
X' represents the —CH$_2$—COOH, CH$_2$—COOZ', —CH$_2$CH$_2$—COOH or —CH$_2$CH$_2$—COOZ' group, or a hydrogen atom,
Y' represents —COOH, —COOZ', or the group —CH$_2$—CHOH—SO$_3$H or CH$_2$—CHOH—SO$_3$Z',
Z' represents an ion resulting from an alkali metal or alkaline-earth metal, such as sodium, an ammonium ion or an ion resulting from an organic amine,
R'$_a$ represents a $C_{10}$ to $C_{30}$ alkyl or alkenyl group of an acid R'$_a$—COOH which is preferably present in coconut oil or in hydrolysed linseed oil, or an alkyl group, especially a $C_{17}$ group, and its iso form, or an unsaturated $C_{17}$ group.

These compounds of formula (A$_1$) or (A$_2$) are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of the cocoamphodiacetate sold by the company Rhodia under the trade name Miranol® C2M Concentrate.

(A$_3$)

wherein,
Y" represents the group —COOH, —COOZ", —CH$_2$—CH(OH)SO$_3$H or the group —CH$_2$CH(OH)SO$_3$—Z";
$R_d$ and $R_e$ represent, independently of each other, a $C_1$-$C_4$ alkyl or hydroxyalkyl radical;
Z" represents a cationic counterion derived from an alkali metal or alkaline-earth metal, such as sodium, an ammonium ion or an ion derived from an organic amine;
$R_a$" represents a $C_{10}$-$C_{30}$ alkyl or alkenyl group of an acid $R_a$"—COOH which is preferably present in coconut oil or in hydrolysed linseed oil;
n and n' denote, independently of each other, an integer ranging from 1 to 3.

Among the compounds of formula (A$_3$), mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use ($C_8$-$C_{20}$) alkylbetaines such as cocoylbetaine, ($C_8$-$C_{20}$) alkylamido($C_3$-$C_8$) alkylbetaines such as cocoylamidopropylbetaine, and mixtures thereof. More preferentially, the amphoteric or zwitterionic surfactant(s) are chosen from cocoylamidopropylbetaine and cocoylbetaine.

The nonionic surfactants that may be present in the composition of the present invention are especially described, for example, in the *Handbook of Surfactants* by M. R. Porter, published by Blackie & Son (Glasgow and London), 1991, pp. 116-178. They are especially chosen from fatty alcohols, fatty α-diols, fatty ($C_1$-$C_{20}$)alkylphenols and fatty acids, these compounds being ethoxylated, propoxylated or glycerolated and containing at least one fatty chain comprising, for example, from 8 to 18 carbon atoms, the number of ethylene oxide or propylene oxide groups possibly ranging especially from 1 to 200, and the number of glycerol groups possibly ranging especially from 1 to 30.

Mention may also be made of condensates of ethylene oxide and of propylene oxide with fatty alcohols, ethoxylated fatty amides preferably having from 1 to 30 ethylene oxide units, polyglycerolated fatty amides comprising on average from 1 to 5 glycerol groups, and in particular from 1.5 to 4, ethoxylated fatty acid esters of sorbitan containing from 1 to 30 ethylene oxide units, fatty acid esters of sucrose, fatty acid esters of polyethylene glycol, ($C_6$-$C_{24}$) alkylpolyglycosides, oxyethylenated plant oils, N—($C_6$-$C_{24}$)alkylglucamine derivatives, amine oxides such as ($C_{10}$-$C_{14}$)alkylamine oxides or N—($C_{10}$-$C_{14}$) acylaminopropylmorpholine oxides.

Preferably, the additional surfactants are chosen from amphoteric or zwitterionic surfactants, nonionic surfactants and mixtures thereof.

Cosmetically Acceptable Medium

The cosmetic composition, according to the present invention, advantageously comprises a cosmetically acceptable medium.

The term "cosmetically acceptable medium" means a medium that is compatible with human keratin fibres, such as the hair.

The cosmetically acceptable medium can be formed from water or from a mixture of water and one or more cosmetically acceptable solvents chosen from $C_1$-$C_4$ lower alcohols, such as ethanol and isopropanol; polyols and polyol ethers, for instance 2-butoxyethanol, propylene glycol, propylene glycol monomethyl ether, diethylene glycol monoethyl ether and monomethyl ether, and mixtures thereof.

The cosmetic composition, according to the present invention, is advantageously aqueous and comprises water in an amount preferably ranging from 30 to 98% by weight, more preferentially from 50 to 95% by weigh, and better still from 60 to 90% by weight, relative to the total weight of the composition.

Additives

The cosmetic composition according to the present invention may further comprise one or more additive(s) other than the compounds of the invention.

As additives that may be used in accordance with the invention, mention may be made of solid fatty substances different from fatty alcohols such as waxes, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners different from oxyethylenated polymers, opacifiers or nacreous agents, antioxidants, hydroxy acids, fragrances and preserving agents.

Needless to say, a person skilled in the art will take care to select this or these optional additional compound(s) such that the advantageous properties intrinsically associated with the composition according to the invention are not, or are not substantially, adversely affected by the envisaged addition(s).

The above additives may generally be present in an amount, for each of them, of between 0.001% and 20% by weight, relative to the total weight of the composition.

Another objet of the present invention relates to a cosmetic treatment process of keratin materials, in which a composition, as described above, is applied on said keratin materials, eventually followed by a leave-on time and/or a rinsing step.

The present invention also relates to a method for conditioning keratin fibres, especially the hair, which consists in applying to the said keratin fibres, in particular the hair, an effective amount of a composition as described above.

The composition can be used as a pre-wash product, as a leave-on product or both.

When the composition is used as a pre-wash product, the leave-on time may range from a few seconds to overnight application.

After an optional leave-on time, the composition may be removed by rinsing.

Generally, the leave-on time of the composition on the keratin fibres may range from a few seconds to 12 hours, preferably from 5 seconds to 60 minutes and even better still from 10 seconds to 15 minutes, or more better from 10 seconds to 5 minutes.

The composition may be applied to wet or dry keratin materials, specially keratin fibres such as hair.

In the present invention, the term "keratin fibres" denotes human keratin fibres, and in particular human hair.

The example that follows serves to illustrate the invention without, however, being limiting in nature.

In the examples that follow and unless otherwise indicated, the amounts are given as mass percentages of active material relative to the total weight of the composition.

EXAMPLES

Example 1

1. Composition

The following composition (A) was prepared from the ingredients indicated in the table below, the amounts of which are expressed as percent by weight of active matter, relative to the total weight of the composition.

|  | Composition (A) |
|---|---|
| Cetearyl alcohol ($C_{16}/C_{18}$, 30/70) | 4% |
| Behentrimonium chloride | 0.08% |
| Cetrimonium chloride | 0.375% |
| Mineral oil | 1% |
| Glycerin | 0.5% |
| Stearamidopropyl dimethylamine | 0.5% |
| Cetyl dimethicone | 0.5% |
| PEG-45M | 0.005% |
| Coconut oil | 0.1% |
| Fragrances, preserving agents | Qs |
| Water | Qs 100% |

2. Application

The composition (A) thus obtained was then used as a leave-on product and was applied on shoulder length hair showing dry damaged corresponding to a sensitization of 3-3.5 on the sensitization scale. The test was repeated on 6 person and the following properties were observed.

During application, composition (A) provided a good melting sensation and showed a very good distribution from the roots to the ends.

After application, the hair showed a slippery feel (no sticky feel), a very good ease of passing fingers, good smoothness and suppleness, good combing and was easy to detangle.

3. Instrumental Evaluation

Composition (A) was then tested through a sliding test, on dry hair.

Swatches (1 g and 27 cm) of medium bleached Indian hair were washed with a shampoo, rinsed and dried.

Composition (A) was then applied on the swatches according to a ratio of 0.15 g of composition per gram of hair. After 5 minutes, the swatches were dried and tested.

Composition (A) was compared to a commercial rinse off conditioner (rinse off conditioners are known to be high on conditioning attributes like softness and smoothness) and to a placebo. The test was done on 6 swatches for each composition.

A movable swatch, attached to a sliding bench, was caused to move in a horizontal rectilinear manner between two other fixed swatches. The force needed to make the swatch to slide between the 2 others was measured with the aid of an electronic gauge linked to a driving arm. The measurement was made from roots to tips.

The average force (of 6 swatches) was calculated and the evolution of the sliding force was recorded to quantify the surface state (homogeneous or not), along the fibre. The lower the sliding force, the better the cosmetic properties.

The results are assembled in the table below.

|  | Average sliding force (N) | Standard deviation (statistical significance if ≤0.05) |
|---|---|---|
| Commercial rinse off conditioner | 0.36 | 0.01 |
| Composition (A) | 0.38 | 0.01 |
| Placebo (no conditioner) | 0.51 | 0.01 |

The results show that the sliding force of composition (A), leave-on product prepared according to the present invention, is closed to the sliding force of the commercial rinse off conditioner. In addition, the sliding force of composition (A) is significantly lower than the sliding force of the placebo.

Therefore, the composition according to the invention confers very good conditioning properties to the hair.

Example 2

1. Composition

The following composition (B) was prepared from the ingredients indicated in the table below, the amounts of which are expressed as percent by weight of active matter, relative to the total weight of the composition.

|  | Composition (B) |
|---|---|
| Cetearyl alcohol ($C_{16}/C_{18}$, 30/70) | 4% |
| Behentrimonium chloride | 0.08% |
| Cetrimonium chloride | 0.375% |

-continued

|  | Composition (B) |
|---|---|
| Mineral oil | 1% |
| Glycerin | 0.5% |
| Stearamidopropyl dimethylamine | 0.5% |
| Cetyl dimethicone | 0.5% |
| PEG-45M | 0.005% |
| Plant oils | 0.03% |
| Fragrances, preserving agents | Qs |
| Water | Qs 100% |

2. Application

The composition (B) thus obtained was then used as a prewash composition.

3. Instrumental Evaluation

Composition (B) was then tested through a sliding test, on wet and dry hair.

Swatches (1 g and 27 cm) of medium bleached Indian hair were washed with a shampoo, rinsed and dried.

Composition (B) was then applied overnight on the swatches according to a ratio of 0.15 g of composition per gram of hair. The following day, the swatches were washed with a shampoo, rinsed and dried.

The process was repeated three times, resulting in three overnight applications. The swatches were then tested.

Composition (B) was compared to a composition (C), containing 100% of coconut oil, and to a composition (D), containing marketed almond oil. The test was done on 6 swatches for each composition.

Following the protocol described above, the average force (of 6 swatches) was calculated and the evolution of the sliding force was recorded to quantify the surface state (homogeneous or not), along the fibre. The lower the sliding force, the better the cosmetic properties.

The results are assembled in the table below.

|  | Average sliding force (N) on wet hair | Standard deviation | Average sliding force (N) on dry hair | Standard deviation |
|---|---|---|---|---|
| Composition B | 0.64 | 0.01 | 0.34 | 0.01 |
| Composition C | 0.96 | 0.01 | 0.42 | 0.01 |
| Composition D | 1.04 | 0.01 | 0.43 | 0.01 |
| placebo (no composition) | 1.10 | 0.01 | 0.51 | 0.01 |

The sliding force of composition (B), prewash product prepared according to the present invention, is lower than the sliding force of compositions (C) and (D), which contain usual oils.

Therefore, the composition according to the invention confers better conditioning properties to the hair than compositions (C) and (D).

The hair is more nourished and smoother when treated with composition (B), in wet and dry state.

The invention claimed is:

1. A hair conditioning composition comprising:
   from 0.1% to 10% by weight of cetyl dimethicone,
   from 0.001 to 0.5% by weight oxyethylenated polymers chosen from the compounds of formula (II)

$$H(OCH_2CH_2)_zOH \qquad (II)$$

wherein z is an integer ranging from 40 000 to 95 000,
   from 0.5 to 7% by weight of one or more fatty alcohols chosen from cetyl alcohol, stearyl alcohol, or mixtures thereof,
   from 0.05 to 5% by weight of behenyltrimethylammonium chloride or cetyltrimethylammonium chloride,
   wherein all weights are relative to the total weight of the composition.

2. The hair conditioning composition according to claim 1, wherein the fatty alcohols is cetearyl alcohol.

3. The hair conditioning composition according to claim 1, wherein the composition further comprises one or more fatty substances liquid at room temperature (25° C.) and at atmospheric pressure ($1.013*10^5$ Pa), different from the fatty alcohols.

4. The hair conditioning composition according to claim 3, wherein the liquid fatty substances are chosen from $C_6$-$C_{16}$ liquid hydrocarbons, liquid hydrocarbons containing more than 16 carbon atoms, non-silicone oils of animal origin, triglycerides of plant or synthetic origin, fluoro oils, liquid fatty acid and/or fatty alcohol esters other than triglycerides, and mixtures thereof.

5. A method for conditioning hair the method comprising:
   applying on said hair, a hair conditioning composition comprising:
   from 0.1% to 10% by weight of cetyl dimethicone,
   from 0.001 to 0.5% by weight oxyethylenated polymers chosen from the compounds of formula (II)

$$H(OCH_2CH_2)_zOH \qquad (II)$$

wherein z is an integer ranging from 40 000 to 95 000,
   from 0.5 to 7% by weight of one or more fatty alcohols chosen from cetyl alcohol, stearyl alcohol, or mixtures thereof,
   from 0.05 to 5% by weight of behenyltrimethylammonium chloride or cetyltrimethylammonium chloride,
   wherein all weights are relative to the total weight of the composition.

* * * * *